United States Patent [19]
Falkenberg et al.

[11] Patent Number: 5,686,301
[45] Date of Patent: Nov. 11, 1997

[54] CULTURE VESSEL FOR CELL CULTURES

[75] Inventors: Frank W. Falkenberg, Witten; Hans-Otto Nagels, Bovenden; Heinz-Gerhard Kohn, Dransfeld, all of Germany

[73] Assignee: Heraeus Instruments GmbH, Hanau, Germany

[21] Appl. No.: 300,628

[22] Filed: Sep. 2, 1994

Related U.S. Application Data

[63] Continuation-in-part of Ser. No. 115,099, Sep. 2, 1993, Pat. No. 5,449,617.

[30] Foreign Application Priority Data

Jul. 22, 1994 [DE] Germany .................. 9411876 U

[51] Int. Cl.$^6$ .................................. C12M 1/02
[52] U.S. Cl. .................. 435/297.1; 435/286.6; 435/289.1; 422/102
[58] Field of Search ............ 435/289.1, 297.1, 435/286.6, 297.5; 422/113, 118, 102

[56] References Cited

U.S. PATENT DOCUMENTS

| | | | |
|---|---|---|---|
| 3,223,595 | 12/1965 | Brewer | 195/139 |
| 4,276,384 | 6/1981 | Mueller | 435/297.2 |
| 4,661,455 | 4/1987 | Hubbard | 435/240 |
| 4,661,458 | 4/1987 | Berry et al. | 435/284 |
| 4,717,668 | 1/1988 | Keilman et al. | 435/296 |
| 4,720,462 | 1/1988 | Rosenson | 435/286.6 |
| 4,734,372 | 3/1988 | Rotman | 435/292.2 |
| 4,748,124 | 5/1988 | Vogler | 435/240.241 |
| 4,839,046 | 6/1989 | Chandler | 435/297.2 |
| 4,959,322 | 9/1990 | Sakai | 435/311 |
| 4,978,616 | 12/1990 | Dean, Jr. et al. | 435/70.3 |
| 4,988,623 | 1/1991 | Schwarz et al. | 435/286 |
| 5,026,650 | 6/1991 | Schwarz et al. | 435/286 |
| 5,110,741 | 5/1992 | Ohi et al. | 435/284 |
| 5,153,131 | 10/1992 | Wolf et al. | 435/240.24 |
| 5,155,034 | 10/1992 | Wolf et al. | 435/240.24 |
| 5,155,035 | 10/1992 | Schwarz et al. | 435/240.24 |
| 5,288,631 | 2/1994 | Baumgartner et al. | 435/240.242 |
| 5,376,548 | 12/1994 | Matsuo et al. | 435/297.2 |
| 5,449,617 | 9/1995 | Falkenberg et al. | 435/240.25 |

FOREIGN PATENT DOCUMENTS

| | | |
|---|---|---|
| WO 90/05179 | 5/1990 | WIPO. |
| WO 91/02555 | 3/1991 | WIPO. |

OTHER PUBLICATIONS

Rotary Cell Culture News, Issue No. 1, Apr. 1994, pp. 1–4.
Synthecon, Inc. 1994 Catalog of Products.
*NASA Tech Briefs, Inventors of the Year, Johnson Team's Biotech Breakthrough*, Mar. 1992, vol. 16, No. 3.

(List continued on next page.)

*Primary Examiner*—Lien Tran
*Attorney, Agent, or Firm*—Workman, Nydegger & Seeley

[57] ABSTRACT

A cell culture vessel which permits gentle but vigorous intermixing and suspending of the cell culture during rotation. The culture vessel features a cell mixing and suspending device combined with a gas exchange membrane such that ample gas exchange occurs without the need to feed oxygen to the cells. The cell mixing and suspending device comprises a baffle system having at least one, and preferably more than one, mixing elements integral with the gas exchange membrane. Movement of the culture vessel, such as for example by rolling, shaking or swirling, moves the mixing elements such that the cells which are to be cultivated are gently intermixed and stably suspended within the cell culture chamber. Pressure variations within the cell culture vessel are accommodated by pressure equalizing device. The pressure equalizing device preferably comprises pressure sheathing made of gas permeable material positioned to form at least a portion of the outer wall of the supply chamber. The pressure sheathing compresses to accommodate increased pressure within the supply chamber. Moreover, the gas permeable material permits additional gas exchange to occur through the supply chamber. Mixing of the nutrient medium is accomplished during movement of the cell culture vessel by way of the extending pressure finger.

20 Claims, 4 Drawing Sheets

OTHER PUBLICATIONS

*Medical Research System*, pp. 56–57, Spinoff, 1993, NASA Publication.

Lewis, Marian L. et al., *The Rotary Cell Culture System, A New Dimension for Tissue Culture*, Journal of Cellular Biochemistry 51, pp. 265–273 (1993).

Spaulding, et al., *Viewpoint, Advances in Cellular Construction*, Journal of Cellular Biochemistry, (Mar. 1993), vol. 51, pp. 249–251.

Stephens, T. *NASA Allies Tout Biomedical Spinoffs*, The Journal of NIH Research, (Dec. 1991) vol. 3, pp. 28–31.

Beardsley, T., *Shear Bliss, A Bioreactor Grows Cells That Resemble Real Tissue*, Scientific American, (Feb. 1992) p. 27.

Weichert, et. al, In Vitro Production of Monoclonal Antibodies in High Concentration in a New and Easy to Handle Modular Minifermenter, Proceedings of the "World Congress on Alternativess and Animal Use in the life Sciences", Nov. 14–19, 1993, Baltimore, MD/USA.

Falkenberg, et. al, A Simple and Inexpensive High Density Dialysis Tubing Cell Culture System for the In Vitro Production of Monoclonal Antibodies in High Concentration, Journal of Immunological Methods, 165 (1993) 193–206.

1992 Fisher Product Catalog.

CULTURE VESSEL FOR CELL CULTURES

BACKGROUND OF THE INVENTION

1. Related Applications

A claim for priority of German Utility Model Application, G 94 11 876.0, filed Jul. 22, 1994, incorporated herein by reference, is made for this application. In addition, this application is a continuation-in-part of U.S. application Ser. No. 115,099 filed Sep. 2, 1993, now U.S. Pat. No. 5,449,617 incorporated herein by reference.

2. The Relevant Technology

The present invention concerns a culture vessel for cell cultures with a cell culture chamber which accommodates the cell culture, and with a supply chamber which accommodates a nutrient medium, and with a dialysis membrane which is arranged between the cell culture chamber and the supply chamber, whereby nutrient substances are transported through the dialysis membrane from the supply chamber and into the cell culture chamber and metabolic products are transported away from the cell culture chamber through the dialysis membrane and into the supply chamber, and with a gas exchange membrane which partly circumscribes the cell culture chamber and which is permeable to gas.

Such a culture vessel is known from U.S. Pat. No. 5,153,131, the '131 patent, incorporated herein by reference. The culture vessel described in the '131 patent has an annular cell culture chamber which is capable of rotation about its horizontal axis whereby one side of the circular ring is covered by a gas-permeable, planar, silicone membrane and the other side is covered by a dialysis membrane. In order to avoid shear forces, which act on the cell culture during rotation of the cell culture chamber, the cell culture is not homogeneously mixed. It is precisely in the case of high cell densities, however, that it is necessary to keep the cells in the most stable possible suspension for adequate supplying of the cell culture with nutrient substances and with oxygen. In order to ensure this, the distance between the dialysis membrane and the gas-permeable silicone membrane in the '131 culture vessel is limited to less than 1 inch but preferably not less than 0.25 inch. A supply chamber for accommodating the nutrient medium is arranged next to the dialysis membrane whereby a mixing sphere is provided in the nutrient medium for mixing the medium which is supplied.

Using the known '131 device, cell cultures such as, for example, hybridoma cells, can be produced with high cell densities. During cultivation, however, the distances from the individual cells to the membrane walls change only a little and it is this small maximum distance which ensures adequate exchange of gas and feeding of nutrients to the cell culture. With a given outer diameter, this small maximum distance limits the volume of the cell culture which can be cultivated.

In a conventional incubator atmosphere, pressure variations arise during the cultivation of cells in closed culture vessels. These pressure variations arise, on the one hand, from the expansion of the air which is enclosed in the container during the heating of the vessels, which have been filled at room temperature, to the usual 37° C. which prevails in the incubator. On the other hand, they also arise as a result of the feature that the nutrient medium usually contains, among other materials, a buffer system which is based on $NaHCO_3$. After filling the supply chamber with such a nutrient medium which is based on a $NaHCO_3$ buffer system, which is usually carried out in a laminar flow sterile work bench, the air bubble which is located above the nutrient liquid normally always consists of atmospheric air and does not contain the elevated $CO_2$ concentration of 5 to 10% which is necessary for cultivation with such nutrient media. As a result of this, the $CO_2$-containing atmosphere with a $CO_2$ content of 5 to 10%, which is inescapably necessary for the stability of such a buffer system, is not adjacent to the $NaHCO_3$ of the nutrient solution. As a result of this, decomposition of the $NaHCO_3$ takes place to produce NaOH and $CO_2$. Whereas the NaOH which is produced leads to alkalinization of the nutrient medium, the $CO_2$ which is produced escapes into the gas atmosphere which is located above the nutrient solution and leads to an additional pressure increase there. In the case of manipulations during cultivation, moreover, pressure variations occur again and again in the culture vessel. In the case of the known '131 culture vessel, these pressure variations produce bulging of both the gas-permeable and dialysis membranes.

SUMMARY AND OBJECTS OF THE INVENTION

An object of the present invention is to provide methods and apparatus permitting ample and uniform gas exchange within a cell culture vessel such that cultivation of high cell densities is achieved without the need for pumping or otherwise feeding gas into the culture vessel. The cell culture vessel of the present invention combines a cell mixing and suspending means with a gas exchange membrane to allow the gas exchange needs of a high cell density culture to be efficiently and consistently met by diffusion of gases to and from the controlled incubator atmosphere. In this manner, ample and uniform supply of oxygen and removal of $CO_2$ is accomplished. In addition, the cell mixing and suspending means ensures ample supply of nutrients and removal of metabolic waste products through a dialysis membrane separating the cell culture from a nutrient medium.

Another object of the present invention is to provide methods and apparatus permitting consistent and reproducible growth of high cell densities within a cell culture vessel. The cell culture vessel of the present invention comprises pressure equalization means to minimize distortion of the gas exchange and dialysis membranes in response to pressure variables due to gas generation within the nutrient medium.

The cell culture vessel of the present invention features a cell mixing and suspending means combined with a gas exchange membrane. The cell mixing and suspending means comprises a baffle system having at least one, and preferably more than one, mixing elements integral with the gas exchange membrane. Movement of the culture vessel, such as for example by rolling, shaking or swirling, moves the mixing elements such that the cells which are to be cultivated are gently intermixed and stably suspended within the cell culture chamber. For a given volume of the cell culture chamber, the degree of intermixing is, in essence, dependent in this regard on the number and the size of the mixing elements. In order to ensure adequate intermixing of larger cell culture chamber volumes, too, the number and size of the mixing elements can be modified with ease. In this way, the distances of the cells from the membrane walls vary continually.

Since the mixing elements are firmly connected to the gas exchange membrane, they directly follow the movement of the cell culture vessel. Since the cell culture itself also follows the course of this movement, a constantly unidirectional movement of the mixing elements and the cell culture is capable of being set up. As a result of this, the cell culture is held very gently in suspension and the shear forces which act on the cell culture during intermixing are kept low.

Pressure variations within the cell culture vessel of the present invention are accommodated by pressure equalizing means. The pressure equalizing means preferably comprises pressure sheathing made of gas permeable material positioned to form at least a portion of the outer wall of the supply chamber. The pressure sheathing compresses to accommodate increased pressure within the supply chamber. Moreover, the gas permeable material permits additional gas exchange to occur through the supply chamber.

These and other objects and features of the present invention will become more fully apparent from the following description and appended claims, or may be learned by the practice of the invention as set forth hereinafter.

BRIEF DESCRIPTION OF THE DRAWINGS

Examples of embodiments of the invention are shown in the drawing and are elucidated in more detail below. The following aspects are shown schematically in the drawing.

DETAILED DESCRIPTION OF THE PREFERRED EMBODIMENTS

Figure 1:
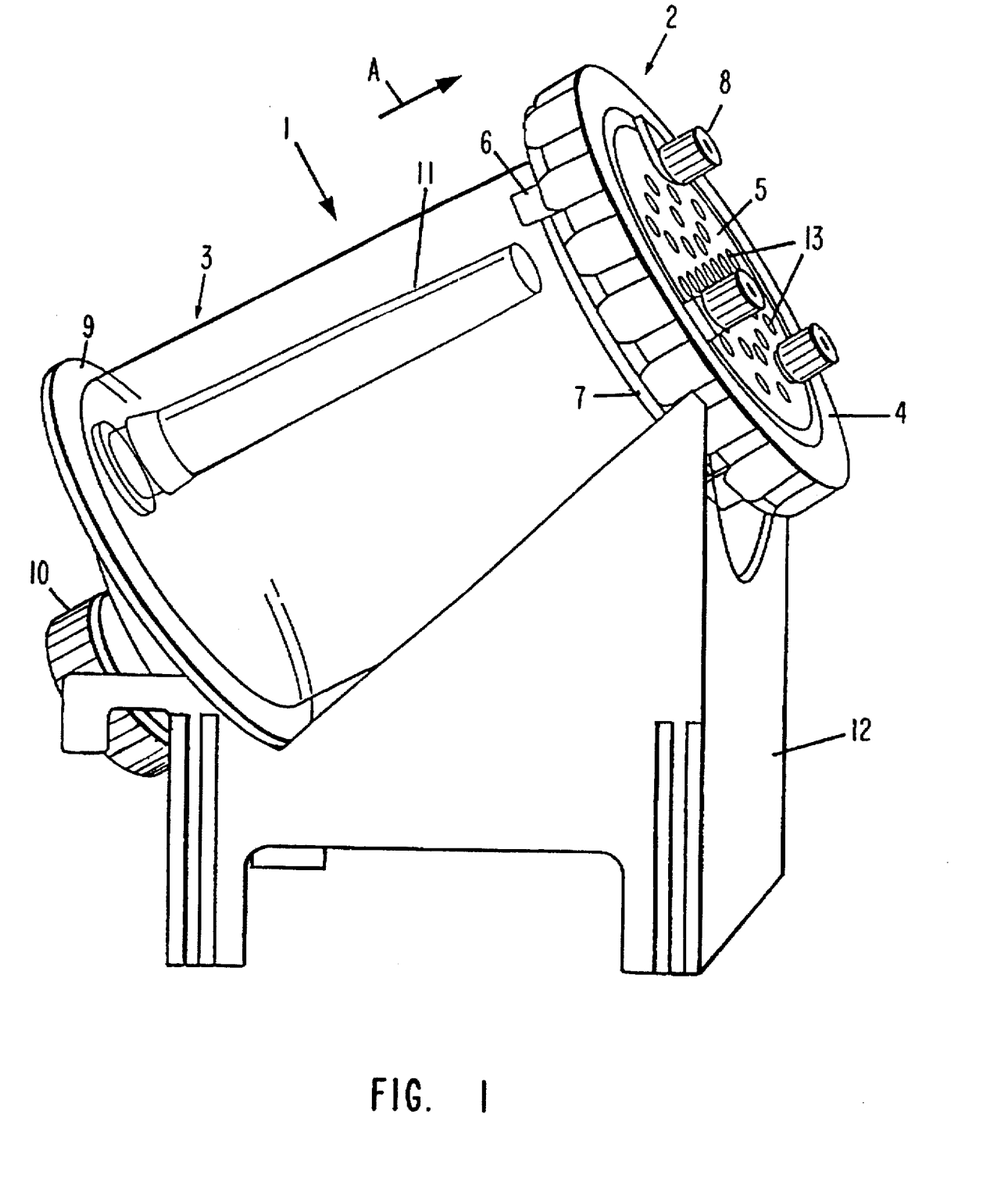
FIG. 1 shows a side view of a culture vessel for cell cultures in accordance with the invention which is arranged on a stand.

In FIG. 1, the reference number 1 is assigned to a culture vessel, in accordance with the invention, in its entirety. The culture vessel may conveniently be placed on a stand 12 when desired. The culture vessel 1, which is essentially cylindrical in shape, is constructed in a modular fashion from a culture chamber 2 and a supply chamber 3. The culture chamber 2 is constructed in the form of a circular ring 4 which is approximately 1 cm high and which is preferably made from a stable plastic. The outward-facing side of the circular ring is covered by a gas exchange membrane 5 having a thickness of about 0.2 mm. The opposite side of the circular ring, which faces the supply chamber 3, is covered by a dialysis membrane 23 (shown in FIGS. 3, 4 and 5). In order to hold the culture chamber 2 on the supply chamber 3, the circular ring 4 is provided with snap-type hooks 6 which lock into position by means of a peripheral circular bulge 7 on the upper edge of the supply chamber 3. In this way, a sealing ring 34 (shown in FIG. 5) ensures the connection of the culture chamber 2 and the supply chamber 3 in a gas-tight and liquid-tight manner.

Filling of the culture chamber 2 with a cell suspension takes place by means of openings 28 (shown in FIG. 5), preferably having Luer-lock connections, which are capable of being closed by means of caps 8. In order to fill the supply chamber 3, it is provided with a filling aperture which is capable of being closed with a screw cap 10. The supply chamber 3 is preferably constructed with a tubular pressure finger 11, described in more detail below. The lower edge of the supply chamber 3 is provided with a peripheral edge 9 projecting outward over the cylindrical surface of the supply chamber to permit rolling of the cylinder. The circular ring 4 of the culture chamber 2 is constructed with a smooth peripheral edge, which also projects outward over the cylindrical surface of the supply chamber 3 and thereby provides another rolling edge. When rolling about its longitudinal axis, the culture vessel 1 rests only on the rolling edge 9 and the peripheral edge of the circular ring 4. Accordingly, the cylindrical surface of the supply chamber is not stressed in this regard.

In accord with the present invention, the gas exchange membrane 5 is provided with an integral baffle system comprising at least one mixing element to provide gentle but vigorous intermixing and suspension of the cells during cultivation. In particular, it has proven especially valuable in practice to construct the mixing element or the mixing elements and the gas exchange membrane in the form of a single unit. As a result of this, it is possible to construct the mixing element or the mixing elements from a material which is permeable to gas and thus provides for gas exchange between the cell culture chamber and the atmosphere which surrounds it. In addition, crevices and edges between the gas exchange membrane and the mixing elements are avoided as a result of unitary construction, as also are the means of attachment, which are optionally required for attaching the mixing elements, whereby adequate and uniform intermixing would not be possible. Suitable materials both for the gas exchange membrane and for the mixing element or the mixing elements are silicone and polytetrafluoroethylene.

The gas permeable membrane of the preferred embodiment as depicted in FIG. 1 comprises a generally flat outward surface which has been constructed with a plurality of hollow knobs 13, open toward the outside, which are round in cross section and which project into the culture chamber 2 to effect intermixing within the cell culture chamber. As described above, the knobs are formed integrally with the gas permeable membrane. Because of their large outward-facing surface area, such knobs, contribute both to the effective mixing of the cell culture and also simultaneously to supplying the suspended cells with oxygen and carrying off the $CO_2$ which is formed as a metabolite. The gas exchange which is brought about through the outward surface area of the knobs, which is open to the surrounding atmospheric gases, is especially rapid and effective since the knobs project into the cell culture chamber and the gases which diffuse through their walls are removed directly from within the midst of the interior of the cell culture ($CO_2$) or, as the case may be, they are admitted directly into the cell culture ($O_2$).

In practice, mixing elements in the form of inwardly projecting knobs which are connected by at least one bridging component, which also projects into the cell culture chamber, have proven to be especially favorable. Such mixing elements bring about intensive mixing without inducing high shear forces in the cell culture. As a result, more effective gas exchange is achieved with more effective intermixing. Mixing takes place especially effectively as a result of such tubularly constructed mixing elements. At the same time, the knobs are able to contribute to a more effective supply of oxygen to the cell culture. In order to achieve effective intermixing and, at the same time, optimal supplying of gas, it is favorable to select the height of the knobs which project into the cell culture chamber be such that the inward flat terminal surface of the knob reaches near to the opposite boundary of the cell culture chamber which can, for example, be formed by the dialysis membrane. It has proven to be especially favorable in practice to construct the gas exchange membrane to have inwardly projecting knobs whereby the size, height and distribution of the knobs are selected in such a way that every point within the cell culture chamber is separated from the gas exchange membrane by not more than 8 mm or, preferably, by not more than 5 mm.

It has proven to be especially advantageous in practice to arrange the projecting knobs and the interconnecting bridging components to substantially subdivide the cell culture chamber into individual chambers. Subdivision into individual chambers brings about the feature that the cell culture mixture cannot accumulate at certain locations within the cell culture chamber for example, on the bottom in the case of rolling cultivation but is more uniformly distributed within the cell culture chamber. In this regard, however, it is not necessary that the individual chambers be rigorously separated from one another. On the contrary, a certain amount of exchange between the individual chambers is desirable. This can be achieved as a result of the feature that the bridging components are constructed such that the depth of projection into the culture chamber is slightly less than the depth of projection attained by the projecting knobs.

Figure 2:
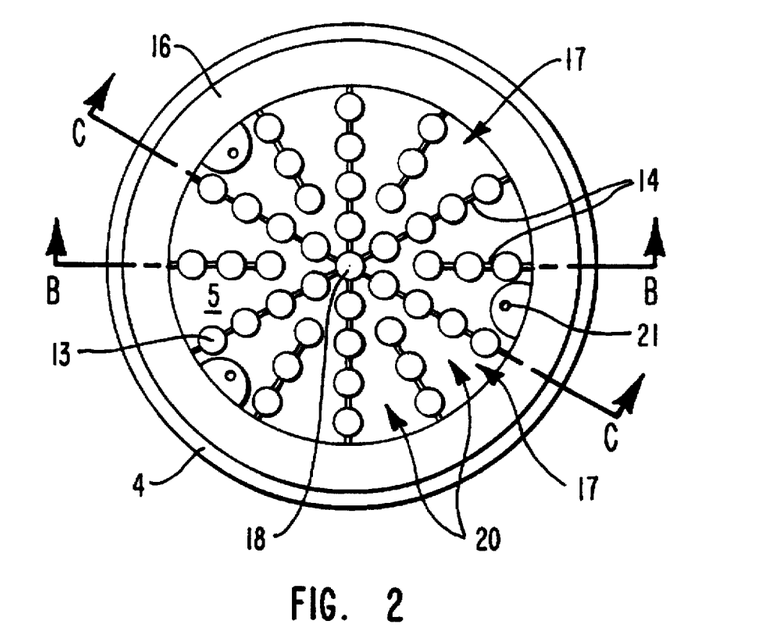
FIG. 2 shows a view from above into a cell culture chamber in the direction of the arrow A in FIG. 1.

One form of embodiment of the culture vessel has proven to be especially valuable in practice is illustrated in FIG. 2 which is a view of the production chamber 2 from the supply chamber side as shown by the arrow A in FIG. 1. The dialysis membrane 23 which separates the supply chamber 3 and the production chamber 2 is not shown. As described above, the gas exchange membrane 5 comprises a plurality of inwardly projecting knobs 13. The knobs are interconnected by bridging components 14. The knobs 13 are also connected to the edge 16 of the gas exchange membrane 5 by means of bridging components 14. A portion of the knobs are connected to one another at a communal point 18 and run outward from there in ray-like form in the direction of the circular ring 4 which circumscribes the cell culture chamber. It can be seen that this configuration subdivides the culture chamber 2 into several individual chambers 17. The individual chambers 17 which are produced in this way may be further subdivided into interconnecting semi-chambers 20 by additional knobs 13 also connected by bridging components 14 but which do not connect to the central point 18. Also shown are the filling openings 21 through which the cell suspension is introduced into the culture chamber 2.

As a result of the preferred configuration illustrated in FIG. 2, the feature is achieved that cells which deposit on the bottom in the in the case of rolling cultivation are carried upward in a scoop-like manner with every rotation along a curved path in the course of rotation and, in essence, drift downward again freely and without the action of mechanical forces. As a result of this, the cell culture is held in suspension in a particularly gentle fashion. In this way, a more uniform distribution of the cells which are to be cultivated can be achieved in the cell culture chamber as a result of the subdivision of the volume of the cell culture chamber into several small individual chambers and, hence, especially effective intermixing is achieved. As a result, intensive, yet gentle, mixing is made possible.

The cylindrically shaped knobs 13 preferably have an external diameter of approximately 7 mm and a height of about 10 mm. Their cylindrical surfaces result, together, in a gas exchange surface which is approximately twice as large as the planar surface of the gas exchange membrane 5 which runs vertically thereto. As discussed above, this dramatically larger surface area greatly enhances gas exchange.

Figure 3:
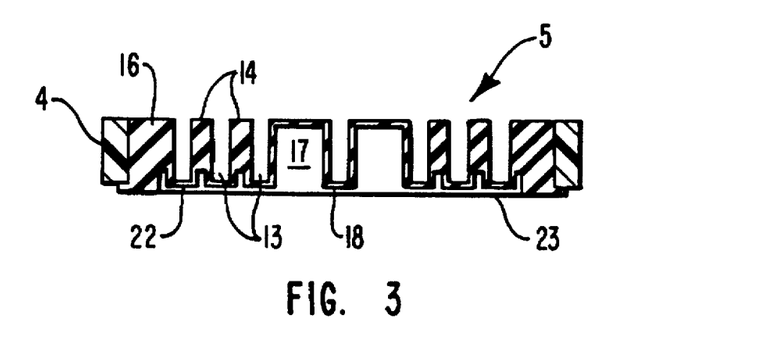
FIG. 3 shows a section through a cell culture chamber along the line B—B in FIG. 2 and through a dialysis membrane which is arranged in front thereof.
Figure 4:
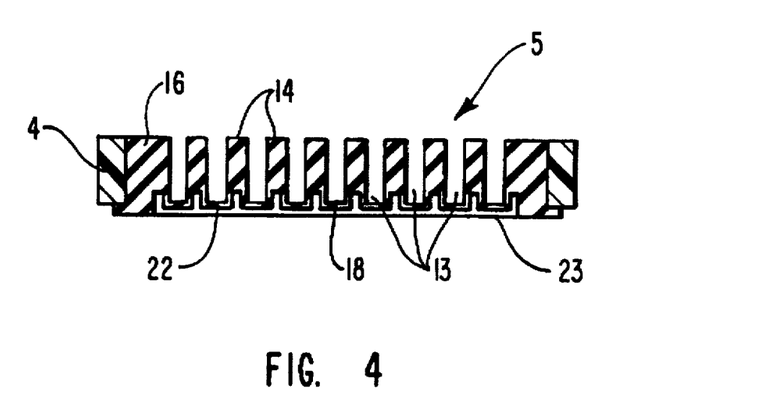
FIG. 4 shows a section through a cell culture chamber along the line C—C in FIG. 2 and through a dialysis membrane which is arranged in front thereof.

To further illustrate the baffle system of the preferred embodiment, FIGS. 3 and 4 provide sectional views of the interconnected knobs and bridging components taken along lines B—B and C—C, respectively, in FIG. 2. FIG. 3 illustrates a sectional view of interconnected knobs 13 not connected at central point 18 while FIG. 4 illustrates a sectional view of knobs 13 which do interconnect with the communal central point 18.

It can be seen in both FIGS. 3 and 4 that the bridging components 14 project inwardly into the culture chamber to a slightly lesser depth than the knobs 13. The knobs are hollow such that an open end faces outward thereby exposing the outward surface area of the knob to the atmosphere while the inward surface extends inwardly near to the dialysis membrane 23. Thus, the inward flat terminal surfaces 22 of the knobs are nearer to the dialysis membrane than the bridging components. It can be seen that this configuration permits a certain exchange of the cell culture between the individual chambers 17.

It can be seen that, on rotating the culture vessel 1, the gas exchange membrane 5 and the integral baffle system comprising the knobs and the bridging components will move in the same direction and cause the cells to be held very gently in a stable suspension. This is so because, in the case of downward movement of the baffle system, the cells in suspension trickle downward on the basis of the force of gravity alone and without mechanical action. Yet, in the case of upward movement, the cells in suspension are carried along and gently lifted.

In a preferred embodiment of the present invention, bulging of the gas exchange membrane and dialysis membrane due to pressure variations caused by gas production within the supply chamber is minimized by means of a pressure-equalizing feature wherein a part of the external wall of the supply chamber is formed from pressure sheathing. The readily deformable pressure sheathing deforms in response to increased pressure and thereby permits pressure equalization. This prevents or reduces deformation of the gas exchange membrane and the dialysis membrane. Accordingly, both the volume of the cell culture chamber and the shape of the membranes remain essentially constant during cell cultivation. The mixing process and, hence, the supplying of nutrients for cell cultivation and the gas exchange process are stabilized as a result.

It has proven to be especially favorable in practice to construct the readily deformable pressure sheathing from a gas permeable material. As a result of this, oxygen can diffuse into the supply chamber by means of the pressure sheathing. From there, it enters the nutrient medium, passes in physically dissolved form through the dialysis membrane and, in this way, contributes to supplying $O_2$ to the cell culture. In the reverse manner, $CO_2$, can be carried out of the cell culture chamber through the supply chamber as well. In practice, silicone and polytetrafluoroethylene have proven suitable as the materials.

One form of embodiment of the culture vessel is preferred in which the pressure sheathing is constructed in the form of a tubular pressure finger which projects into the supply chamber whereby the front side of the pressure finger which projects into the supply chamber is closed and the opposite side thereof is open. Preferably, the pressure finger comprises a gas permeable material such as silicone and a deformable support frame is positioned within the open side of the finger such that the silicone loosely covers the support frame. With such a pressure finger, the required accommodation of pressure can be carried out with ease over the entire length and diameter of the finger. In the case of a cylindrical supply chamber, the pressure finger advantageously extends over the entire length thereof and, in essence, parallels the cylindrical axis of the supply chamber. Because of the large surface area of such a finger configuration, not only is the exchange of gas through the gas-permeable material improved but the support frame permits the projecting finger to act as an effective mixing element for the nutrient medium. In this regard, it is preferable to position the pressure finger such that its longitudinal axis runs next to that of the supply chamber. It is particularly in the case of rolling cultivation in which the longitudinal axis of the supply chamber forms the rotation axis, that this arrangement leads to effective intermixing of the nutrient medium.

Figure 5:
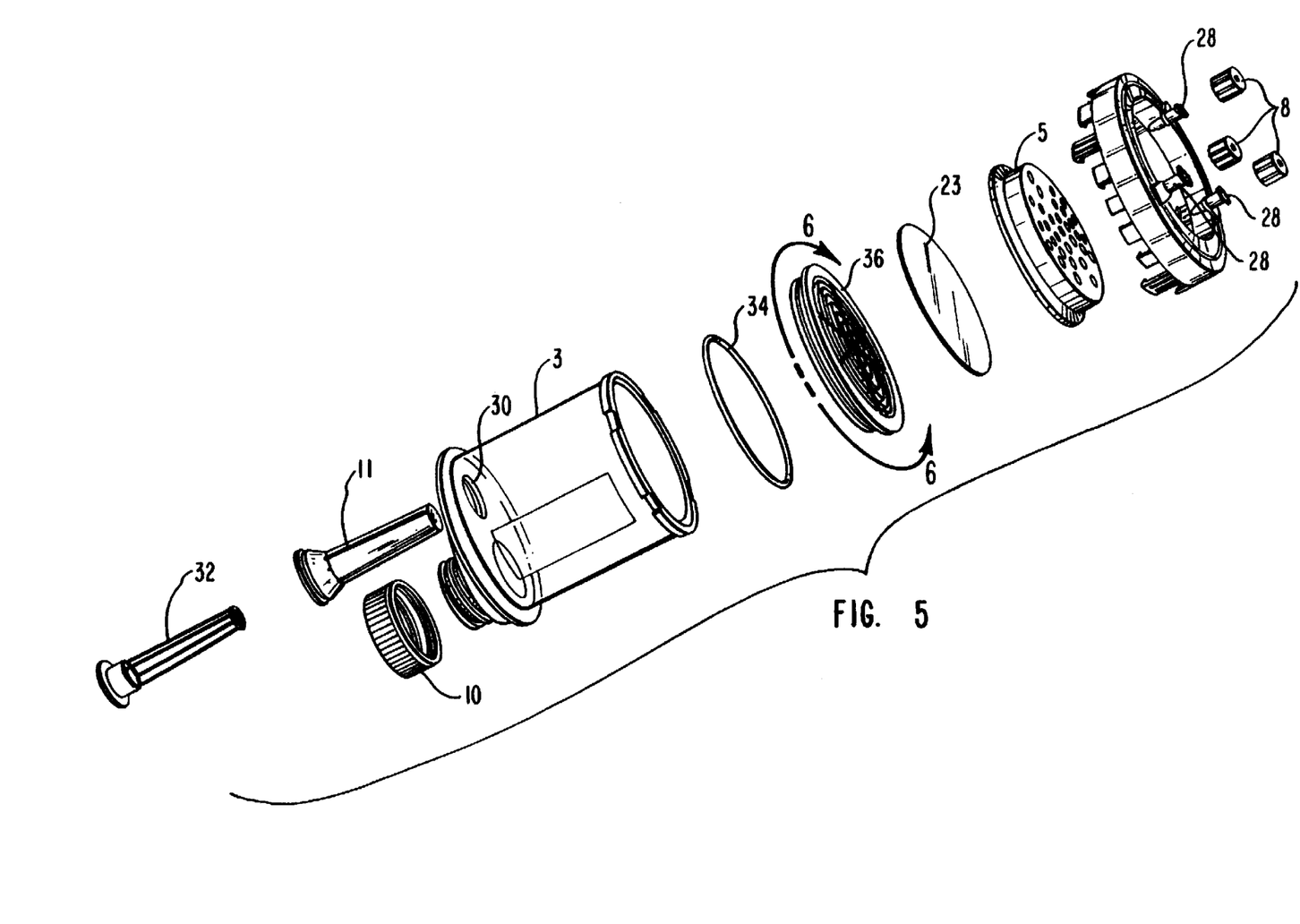
FIG. 5 shows an exploded view of certain components of a cell culture vessel in accord with a preferred embodiment of the present invention.

FIG. 5 illustrates an exploded view of certain components of a preferred embodiment of a cell culture vessel in accord with the present invention. Components shown in FIG. 1 are numbered correspondingly in FIG. 5. Access for filling the supply chamber 3 is provided by an opening sealed with a screw cap 10. Another opening 30 in the supply chamber permits the pressure finger 11, which is preferably made of silicone, to be positioned to extend into the supply chamber 3. The silicone pressure finger loosely covers a support frame 32 constructed to support the pressure finger material in an extended position but still permit gas to diffuse through the pressure finger. The looseness of the fit permits some compression of the silicone pressure finger in response to increasing gas pressure within the supply chamber without deforming the support frame. However, in response to sufficient applied pressure, the support frame can also deform somewhat such that pressure variations can be equalized within the supply chamber either through compression of the silicone pressure finger alone or through compression of both the silicone pressure finger and the support frame. The support frame 32 enhances the mixing ability of the pressure finger by providing a slightly more rigid structure.

It can be seen that the pressure finger accommodates pressure variations which arise during cell cultivation and at the same time permits gas exchange between the supply chamber and the atmosphere of the incubator. The non-centric positioning of the pressure finger outside the rotation axis also serves for better intermixing of the nutrient medium. The length and diameter of the pressure finger are adapted to the expected maximum pressure variations. In the case of a positive pressure inside the supply chamber, the pressure finger becomes compressed. Accordingly, distortion or outward bulging of the dialysis membrane and of the gas exchange membrane, and a resulting change in the volume of the culture chamber and in the mixing conditions, is minimized. In this way, the pressure finger ensures reproducible cell cultivation.

Also shown in FIG. 5 are components associated with the culture chamber of a preferred embodiment of the present invention. As previously described, the culture chamber is constructed in the form of a circular ring 4 wherein the side pointing outward is covered by the gas exchange membrane 5 and the opposite side, facing the supply chamber 3, is covered by the dialysis membrane 23. The outward facing surface of the circular ring 14 comprises openings 28, preferably in the form of Luer-lock connections, for filling the culture chamber and caps 8 for sealing the openings. Sealing ring 34 ensures a gas-tight and liquid-tight attachment between the supply chamber and culture chamber. A support grid 36 is positioned between the dialysis membrane and the supply chamber 3 to add stability to the cell culture vessel and assist in maintaining the size and shape of the dialysis membrane.

Figure 6:
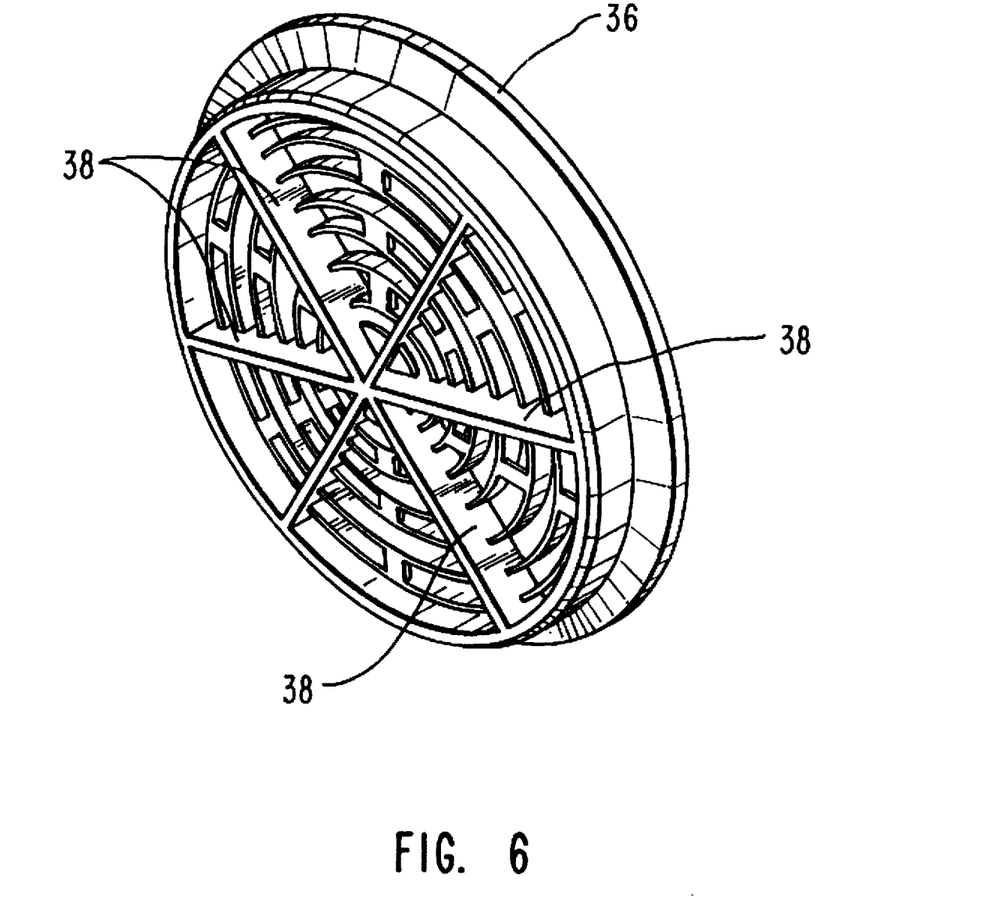
FIG. 6 shows a view of one side of a support grid component of the preferred embodiment of the present invention.

FIG. 6 shows the support grid 36 in greater detail. The support grid is preferably made of plastic or other suitably rigid or semi-rigid material. The side of the support grid which contacts the nutrient medium within the supply chamber preferably has at least one attached mixing element. In a preferred embodiment, the mixing element is formed as integral webs 38 which extend from the surface of the support grid and thereby effect mixing of the nutrient medium during movement of the culture vessel.

To illustrate a preferred method of the present invention, an example of a process for the cultivation of cells will be elucidated in more detail below by reference to the drawings.

Initially, the cells which are to be cultivated are introduced into the culture chamber 2 which has a volume of approximately 35 ml. The significantly larger supply chamber 3, having a volume of approximately 600 ml, is filled with the nutrient medium to the extent of ⅔, so that an air bubble of approximately ⅓ of the volume remains therein. This air bubble serves, on the one hand, for better intermixing of the nutrient medium and, on the other hand, it contributes to gas exchange for cell cultivation.

Neither the cells nor the high molecular weight products which are released from the cells are capable of passing through the semipermeable dialysis membrane 23. Nutrient substances, vitamins, ions and gases which are physically dissolved in the medium, including $O_2$ and $CO_2$ can, by contrast, move from the supply chamber 3 into the culture chamber 2 in a virtually unhindered manner. Because of the approximately 10 fold excess volume of the nutrient medium which is being supplied, the cells are provided with the substances which are necessary for cultivation for an extended period of time which depends on cell density.

At the same time, the acidic, toxic and other metabolites which are released by the cells leave the culture chamber 2 by means of the dialysis membrane 23 and are collected and neutralized in the significantly larger volume of the supply chamber 3.

The oxygen demand of hybridoma cells is of the order of magnitude of 5 µg of $O_2$, per $10^6$ cells per hour. In the case of a cell density of $10 \times 10^6$ cells/ml, as can readily be achieved in culture vessel 1 in accordance with the invention, the oxygen demand of the $350 \times 10^6$ cells in the 35 ml in culture chamber 2 mounts to about 1.75 mg/h. This demand is covered by the inward diffusion of atmospheric oxygen into the culture chamber 2 from the atmosphere of the incubator through the very thin gas exchange membrane 5. The $CO_2$ which is produced in correspondingly large quantities by the cells leaves the culture chamber 2 along the same route. The $CO_2$ which is produced by the cells can "be exhaled" by means of the gas exchange membrane 5 in a similar way, to a certain extent, to that in a lung.

The removal of $CO_2$ from the culture vessel is additionally promoted by the feature that $CO_2$ which is both physically dissolved, and, in the form of $NaHCO_3$, can also pass through the dialysis membrane 23 and can, in this way, move into the supply chamber 3 from the culture chamber 2. Then, it can also "be exhaled" from the supply chamber 3 by means of diffusion through the gas permeable material of the pressure finger 11 which is installed therein.

Atmospheric oxygen also moves from the outside through the pressure finger 11 into the supply chamber 3. The nutrient medium is thereby enriched with oxygen. Then this oxygen in physically dissolved form can also pass through the dialysis membrane 23 into the culture chamber 2.

In order to achieve optimal supply of gas and nutrients and disposal of waste products for high cell density cell cultivation, the cells must be kept constantly in suspension. For an optimal exchange of substances at the dialysis membrane 23 and at the gas exchange membrane 5, both the supply medium and the cell suspension have to be constantly circulated. Thus, the cell culture vessel is subjected to movement and gentle but vigorous intermixing and suspending of the cell culture is achieved by way of the integral baffle system. Mixing of the nutrient medium is accomplished during movement of the cell culture vessel by way of the extending pressure finger. Mixing may also be enhanced by mixing elements projecting into the nutrient medium from a support grid positioned between the supply chamber and the dialysis membrane. Optimal cultivation of high cell densities is obtained with a culture vessel in which these features are combined.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A cell culture vessel comprising:
   a cell culture chamber for receiving a cell culture;
   a supply chamber for receiving a nutrient medium;
   a dialysis membrane interposed between the cell culture chamber and the supply chamber whereby nutrients are separated from the cell culture chamber but may be transported from the supply chamber through the dialysis membrane into the cell culture chamber and whereby metabolic waste products may be transported out of the cell culture chamber through the dialysis membrane and into the supply chamber;
   a gas exchange membrane interposed between the cell culture chamber and a source of oxygen and which is permeable to gas; and
   cell mixing means for ensuring intermixing and suspension of the cells within the cell culture chamber, said mixing means comprising:
   at least one mixing element which will generate shear forces when the cell culture vessel is rotated, said mixing element including bridging components which project into the cell culture chamber and wherein the mixing element further comprises a plurality of regions having an inward surface area which projects into the cell culture chamber.

2. A cell culture vessel in accordance with claim 1 wherein the mixing element is formed integrally with the gas exchange membrane.

3. A cell culture vessel in accordance with claim 1 wherein the regions are hollow knobs having an inward circular side surface and an inward flat terminal surface projecting into the cell culture chamber.

4. A cell culture vessel in accordance with claim 3 wherein the hollow knobs further comprise outwardly facing open end and an outward surface area, said outward surface area having a circular side surface and a flat terminal surface which are exposed to the atmosphere surrounding the cell culture vessel.

5. A cell culture vessel in accordance with claim 4 wherein a portion of the inward circular side surfaces of the hollow knobs are connected to each other by the bridging components to thereby form a plurality of interconnected knobs.

6. A cell culture vessel in accordance with claim 5 wherein the hollow knobs and bridging components subdivide the cell culture chamber into individual chambers which are substantially separate from one another.

7. A cell culture vessel in accordance with claim 6 wherein the cell culture chamber is circumscribed by a circular wall covered on one surface by the gas exchange membrane and the other surface by the dialysis membrane.

8. A cell culture vessel in accordance with claim 7 wherein a portion of the interconnected knobs have a webbing configuration such that rows of interconnected knobs and bridging components begin at spaced apart points near the circular wall and converge at a central point on the gas permeable membrane.

9. A cell culture vessel in accordance with claim 8 wherein the knobs are of a selected size, height and distribution such that every point within the cell culture chamber is separated from the gas exchange membrane by not more than 8 mm.

10. A cell culture vessel in accordance with claim 8 wherein the knobs are of a selected size, height and distribution such that every point within the cell culture chamber is separated from the gas exchange membrane by not more than 5 mm.

11. A cell culture vessel in accordance with claim 7 further comprising a support grid interposed between the dialysis membrane and the supply chamber such that the nutrient medium contacts one surface of the support grid, said support grid having at least one mixing element attached to said surface.

12. A cell culture vessel comprising:
   a cell culture chamber for receiving a cell culture;
   a supply chamber for receiving a nutrient medium, said supply chamber having an outer wall, said outer wall comprising pressure sheathing that deforms to accommodate pressure variations which arise in the supply chamber during cell cultivation;
   a dialysis membrane interposed between the cell culture chamber and the supply chamber whereby nutrients are separated from the cell culture chamber but may be transported from the supply chamber through the dialysis membrane and into the cell culture chamber and whereby metabolic waste products may be transported out of the cell culture chamber through the dialysis membrane and into the supply chamber; and
   a gas exchange membrane interposed between the cell culture chamber and a source of oxygen which is permeable to gas.

13. A cell culture vessel in accordance with claim 12 wherein the pressure sheathing comprises a gas permeable material to permit an exchange of gas between the supply chamber and the atmosphere which surrounds the culture vessel.

14. A cell culture vessel in accordance with claim 13 wherein at least one part of the pressure sheathing is constructed in the form of an elongated hollow tube member having an inward-facing side which projects into the supply chamber and an outward-facing side having an open end such that said outward-facing side is exposed to the atmosphere surrounding the supply chamber.

15. A cell culture vessel in accordance with claim 14 wherein the supply chamber is constructed in cylindrical form and the elongated hollow tube member extends essentially parallel to the cylindrical axis of the supply chamber over substantially the entire length of the supply chamber such that the longitudinal axis of the elongated hollow tube member is adjacent to the longitudinal axis of the supply chamber.

16. A cell culture vessel in accordance with claim 15 further comprising a deformable support frame which fits loosely within the open end of the elongated hollow tube member.

17. A cell culture vessel comprising:

a cell culture chamber for receiving a cell culture;

a supply chamber for receiving a nutrient medium, said supply chamber having an outer wall, said outer wall comprising pressure sheathing that deforms to accommodate pressure variations which arise in the supply chamber during cell cultivation;

a dialysis membrane interposed between the cell culture chamber and the supply chamber whereby nutrients are separated from the cell culture chamber but may be transported from the supply chamber through the dialysis membrane and into the cell culture chamber and whereby metabolic waste products may be transported out of the cell culture chamber through the dialysis membrane and into the supply chamber; and a gas exchange membrane interposed between the cell culture chamber and a source of oxygen which is permeable to gas, said gas exchange membrane comprising cell mixing means for ensuring intermixing and suspension of the cells within the cell culture chamber.

18. A pressure-accommodating chamber comprising an outer wall, said outer wall comprising pressure sheathing that deforms to accommodate pressure variations within the chamber, said pressure sheathing comprising a gas permeable material to permit an exchange of gas between the chamber and the surrounding atmosphere and wherein at least one part of the pressure sheathing is constructed in the form of an elongated hollow tube member having an inward-facing side which projects into the chamber and an outward-facing side having an open end such that said outward-facing side is exposed to the atmosphere surrounding the supply chamber.

19. A pressure-accommodating chamber in accordance with claim 18 wherein the chamber is constructed in cylindrical form and the elongated hollow tube member extends essentially parallel to the cylindrical axis of the chamber over substantially the entire length of the chamber such that the longitudinal axis of the elongated hollow tube member is adjacent to the longitudinal axis of the chamber.

20. A pressure-accommodating chamber in accordance with claim 19 further comprising a deformable support frame which fits loosely within the open end of the elongated hollow tube member.

* * * * *